US012678199B2

(12) United States Patent
Zastrozna et al.

(10) Patent No.: US 12,678,199 B2
(45) Date of Patent: *Jul. 14, 2026

(54) SKIN MORPHING AND TENSION DISTRIBUTING SYSTEM FOR EXTERNAL FIXATION AND METHODS OF USE THEREOF

(71) Applicant: DePuy Synthes Products, Inc., Raynham, MA (US)

(72) Inventors: Anna Zastrozna, West Chester, PA (US); John Anastasiadis, Andover, MA (US); Dana Coombs, West Chester, PA (US); Kenneth Kobayashi, West Chester, PA (US); James Amis, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 776 days.

This patent is subject to a terminal disclaimer.

(21) Appl. No.: 17/938,079

(22) Filed: Oct. 5, 2022

(65) Prior Publication Data

US 2023/0044717 A1 Feb. 9, 2023

Related U.S. Application Data

(63) Continuation of application No. 16/590,810, filed on Oct. 2, 2019, now Pat. No. 11,484,345.

(51) Int. Cl.
*A61B 17/66* (2006.01)
*A61B 17/08* (2006.01)
*A61B 17/00* (2006.01)

(52) U.S. Cl.
CPC ............ *A61B 17/66* (2013.01); *A61B 17/085* (2013.01); *A61B 2017/00862* (2013.01); *A61B 2017/00889* (2013.01); *A61B 2017/00951* (2013.01)

(58) Field of Classification Search
CPC ..... A61B 17/60; A61B 17/64; A61B 17/6491; A61B 17/66; A61B 17/08; A61B 17/085;
(Continued)

(56) References Cited

U.S. PATENT DOCUMENTS 4,730,608 A * 3/1988 Schlein ................. A61B 17/66
606/57
5,080,661 A * 1/1992 Lavender .......... A61F 13/00063
606/53
(Continued)

FOREIGN PATENT DOCUMENTS

DE 29880029 U1 7/1999
EP 2550990 A1 1/2013
WO 2013038182 A2 3/2013

OTHER PUBLICATIONS

Ahmad, et al.; "Feasibility Study of Polyurethane Shape-Memory Polymer Actuators for Pressure Bandage Application," Science and Technology of Advanced Materials; (2012), vol. 13, pp. 1-7.
(Continued)

*Primary Examiner* — Eduardo C Robert
*Assistant Examiner* — Michelle C Green
(74) *Attorney, Agent, or Firm* — Dunlap Codding, P.C.

(57) ABSTRACT

Kits and systems are disclosed that include one or more segments of elastically deformable membrane in combination with one or more external fixation members and optionally in combination with one or more tension protector pads. Also disclosed are methods of use of the kits and systems in methods that involve stretching the elastically deformable membrane and applying the stretched membrane to the skin of a patient, and releasing the tension on the membrane, thus causing compression of the skin to which the membrane is applied. The method may further include the optional steps of inserting one or more external fixation members through the membrane/skin combination and into a bone segment,
(Continued)

applying a distraction force to the one or more external fixation members, and adjusting one or more segments of membrane to affect skin tension at a rate that is similar to a rate at which the distraction force is applied.

8 Claims, 9 Drawing Sheets

(58) Field of Classification Search
CPC ..... A61B 2017/081; A61F 2013/00451; A61F 2013/00089; A61F 2013/00361; A61F 2013/00119–00148
See application file for complete search history.

(56) References Cited

U.S. PATENT DOCUMENTS

| | | | |
|---|---|---|---|
| 5,447,492 A * | 9/1995 | Cartmell | A61F 13/0203 |
| | | | 602/41 |
| 7,834,232 B2 | 11/2010 | Rastegar et al. | |
| 8,389,791 B2 | 3/2013 | Gurtner et al. | |
| 9,592,206 B2 | 3/2017 | Walls | |
| 9,913,758 B2 | 3/2018 | Rastegar et al. | |
| 10,123,789 B1 * | 11/2018 | Kennedy | A61B 17/0057 |
| 10,695,237 B1 * | 6/2020 | Sanders, Jr. | A61F 15/006 |
| 11,484,345 B2 * | 11/2022 | Zastrozna | A61B 17/60 |
| 2008/0146982 A1 * | 6/2008 | Rastegar | A61B 17/085 |
| | | | 602/54 |
| 2008/0281324 A1 * | 11/2008 | Webb | A61B 17/60 |
| | | | 128/898 |
| 2009/0318842 A1 * | 12/2009 | Kairinos | A61F 13/0226 |
| | | | 606/59 |
| 2010/0030171 A1 * | 2/2010 | Canada | A61F 13/0223 |
| | | | 604/378 |
| 2016/0213522 A1 * | 7/2016 | Gurtner | A61F 13/0243 |
| 2018/0078686 A1 | 3/2018 | Proctor, Jr. et al. | |
| 2018/0185196 A1 * | 7/2018 | Levinson | A61B 17/32093 |
| 2019/0015255 A1 | 1/2019 | Gurtner et al. | |

OTHER PUBLICATIONS

Kumar, et al.; "Memory Bandage for Functional Compression Management for Venous Ulcers," Fibers; (2016), vol. 4, pp. 1-10.

Kazmers, et al.; "Prevention of Pin Site Infection in External Fixation: A Review of the Literature," Strat Traum Recon (2016), vol. 11, pp. 75-85.

Ferreira, et al.; "Prevention and Management of External Fixator Pin Track Sepsis," Strat Traum Limb Recon (2012). vol. 7, pp. 67-72.

"Biopatch Protective Disk with CHG," Ethicon, Inc. Somerville, NJ; 1 page.

International Search Report, mailed Jan. 11, 2021, in PCT/IB2020/058736, filed Sep. 18, 2020.

U.S. Appl. No. 16/590,810; Office Action dated Mar. 1, 2022, filed Oct. 2, 2019.

U.S. Appl. No. 16/590,810; Amendment and Response to Office Action dated Mar. 22, 2022, filed Oct. 2, 2019.

U.S. Appl. No. 16/590,810; Notice of Allowance dated Jun. 29, 2022, filed Oct. 2, 2019.

* cited by examiner

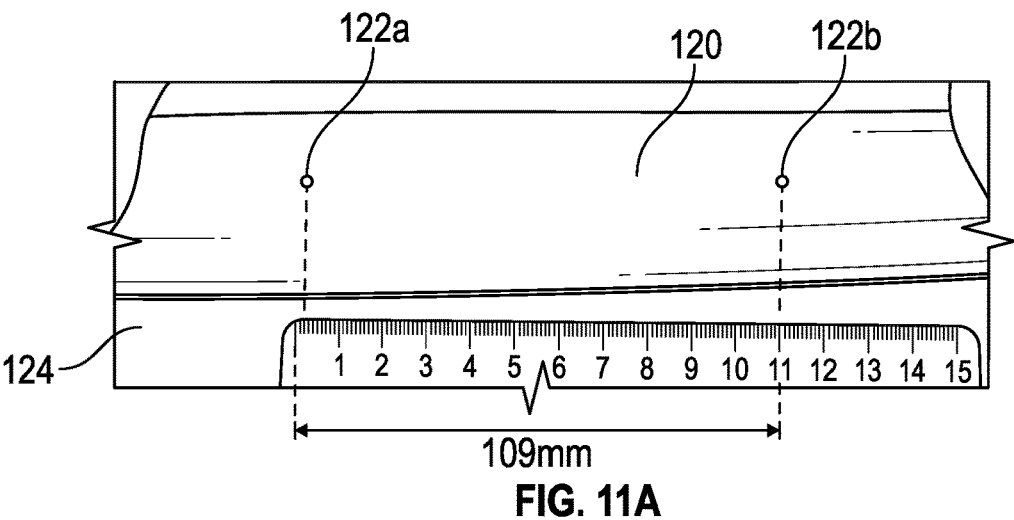
FIG. 11A
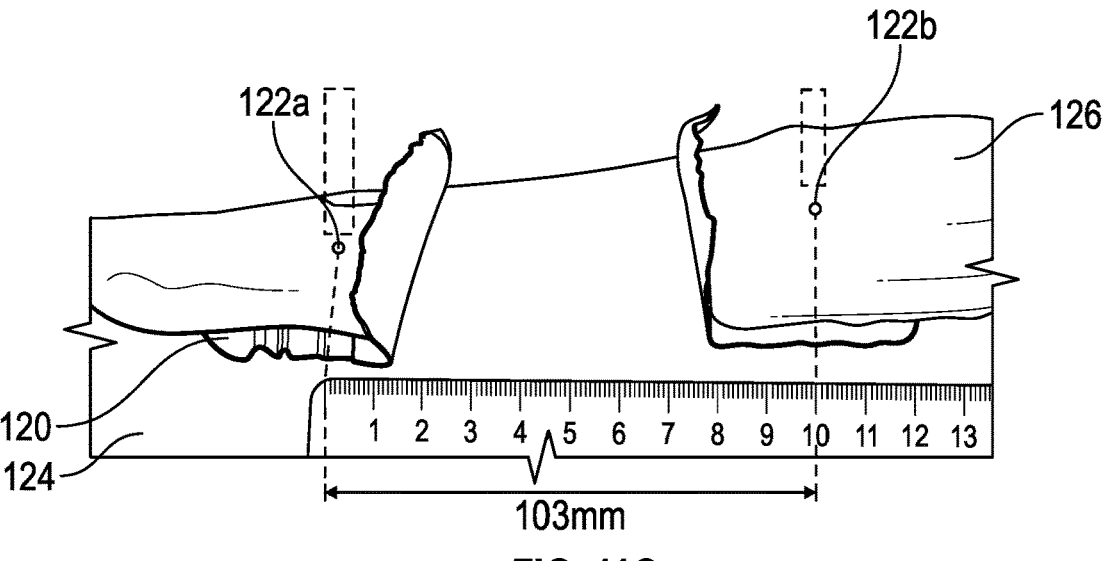
FIG. 11B
FIG. 11C

SKIN MORPHING AND TENSION DISTRIBUTING SYSTEM FOR EXTERNAL FIXATION AND METHODS OF USE THEREOF

CROSS REFERENCE TO RELATED APPLICATIONS/INCORPORATION BY REFERENCE STATEMENT

This application is a continuation of U.S. Ser. No. 16/590, 810, filed Oct. 2, 2019. The entire contents of the above-referenced patent application(s) are hereby expressly incorporated herein by reference.

STATEMENT REGARDING FEDERALLY SPONSORED RESEARCH OR DEVELOPMENT

Not Applicable.

BACKGROUND

Percutaneous devices, such as (but not limited to) pins, screws, and wires, are commonly used in orthopedic procedures to stabilize and/or correct fractures, injuries, and defects. Particular examples of percutaneous devices include (but are not limited to) skeletal traction pins, percutaneous fracture pinning, and external fixation devices. However, these devices can cause excessive skin tension at their insertion sites, and this tension can decrease blood supply and lead to necrosis of the surrounding tissue, thus acting as a 'magnet' for infection at the insertion site.

For example, external fixation of bone fractures commonly involves the long-term use of orthopedic pins inserted into the bone fragments and fixed to the external structure. The pins stress the skin around them during bone distraction or patient movement, often leading to the cutting or tearing of pin tracks in the skin, along with the subsequent infection associated therewith. Indeed, one study reported site infection as the most common complication of external fixation, with an 11.3% to 100% infection rate in the study group (Kazmers et al., (2016) *Strat Traum Limb Recon,* 11:75-85).

Currently, clinicians recommend a variety of techniques to try to prevent pin track infection, including local antiseptics and regular pin site cleaning. Despite aggressive treatments, however, pin track infection is still the most common complication of external fixation. In addition, the risk of pin track infection increases with time; the longer an external fixation pin remains in place, the higher the risk of infection and the more severe the infections become. With more recently developed surgical treatments such as distraction osteogenesis, external fixation pins can remain in place for many months. The success of these distraction osteogenesis procedures depends upon the ability to maintain the fixation pins infection-free for long periods. Pin track infection can decrease the stability of the fixator pin-bone interface, which creates an unsuitable environment for optimal bone healing and can lead to pin loosening, fracture non-union, and chronic osteomyelitis (Ferreira and Marais (2012) *Strategies Trauma Limb Reconstr,* 7(2): 67-72). While soft tissue infection can often be treated effectively with oral antibiotics and local skin treatment, deeper bone infection typically requires removal of percutaneous pins or abandonment of external fixation altogether.

Therefore, there is a need in the art for new and improved devices and methods of using same around the insertion sites of percutaneous devices, to reduce skin tension and the cutting/tearing of skin in response to bone distraction or patient movement, and thus reduce the risk of infection related thereto. It is to such devices, as well as methods of producing and using same, that the present disclosure is directed.

BRIEF DESCRIPTION OF THE DRAWINGS

FIGS. 11A-C contain perspective views illustrating application of a skin morphing and tension distributing system constructed in accordance with the present disclosure to the skin of a patient.

DETAILED DESCRIPTION

Figure 1:
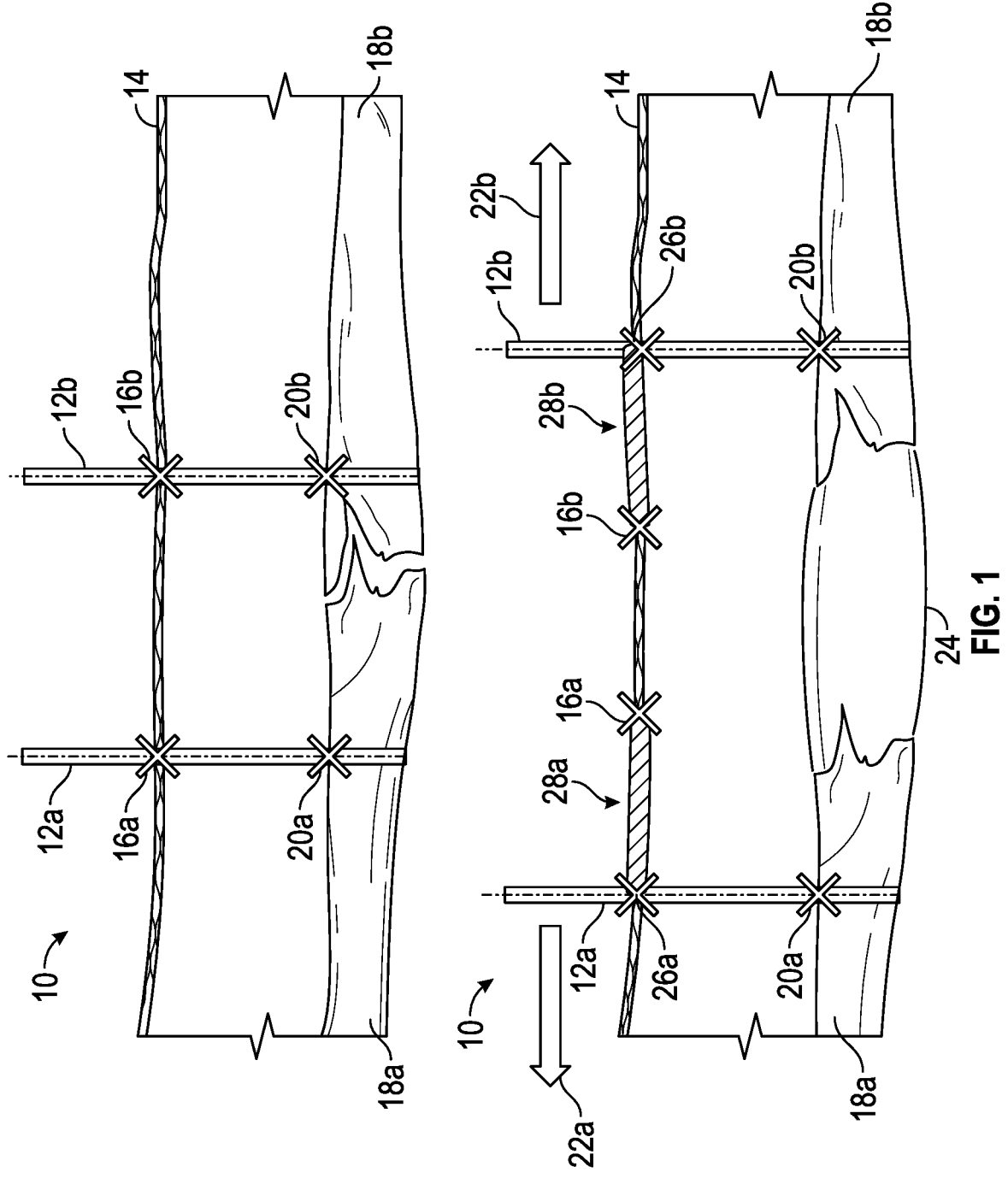
FIG. 1 contains diagrammatic views of the use of a prior art external fixation device and creation of pin tracks during a bone distraction procedure.

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the medical procedures and techniques of, surgery, anesthesia, wound healing, and infectious control described herein are those well-known and commonly used in the art. Standard techniques are used for infection diagnostic and therapeutic applications.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutions and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

The use of ordinal number terminology (i.e., "first," "second," "third," "fourth," etc.) is solely for the purpose of differentiating between two or more items and, unless explicitly stated otherwise, is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps. For example, a process, method, article, or apparatus that comprises a list of elements is not necessarily limited to only those elements but may include other elements not expressly listed or inherently present therein.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example (but not by way of limitation), when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

As used herein, the term "patient" or "subject" is meant to include all organisms, whether alive or dead, including any species having soft tissues and bones. For example, a system according to the inventive concepts disclosed herein may be applied to the skin of a living human, horse, cow, sheep, cat, dog, and the like.

Certain non-limiting embodiments of the present disclosure are directed to a method of reducing a risk of infection, comprising the steps of: (A) applying force to a segment of elastically deformable membrane to stretch the membrane to a stretched length that is greater than an original length of the membrane, wherein the elastically deformable membrane has a bonding material associated with at least a portion of a surface thereof; (B) applying the stretched membrane to a skin of a patient, wherein the bonding material attaches the stretched membrane to the skin; (C) releasing the stretch force on the membrane after application to the skin, thereby causing the skin having the membrane attached thereto to gather/compress; and (D) inserting at least one external fixation member through the skin and tissue of the patient and into a bone of the patient. In one non-limiting embodiment, the at least one external fixation member is inserted through the membrane and skin at a location interior to an end of the membrane (i.e., between the two ends of the membrane). In another non-limiting embodiment, the at least one external fixation member is not inserted through the membrane but rather is inserted through the skin at a location outside of the membrane (for example, for clinical reasons, such as (but not limited to) when an open wound is present).

In certain non-limiting embodiments, the method further comprises the step of: (E) applying at least one distraction force to the at least one external fixation member to move the bone with which the external fixation member is associated. Additionally, the method may further comprise the step of: (F) separating at least a portion of the membrane so as to release a portion of the tension/compression in the skin at a rate that is similar to a rate at which the distraction force is applied. When the method includes steps (E) and (F), the method may further include the step of: (G) repeating steps (E) and (F) over a period of time, thus allowing the skin to move at a rate similar to the external fixation member inserted therethrough. As such, the method provides a mechanism by which to tailor the stretch and release of the skin and provide a "neutral travel zone" that reduces skin tension and the incidence of pin track creation and, as a result, the incidence of pin track infections.

The term "elastically deformable membrane" as used herein refers to any type of membrane or tape known in the art or otherwise contemplated herein that is capable of functioning in accordance with the present disclosure. That is, at least a portion of the elastically deformable membrane should be formed of a material that is capable of being stretched and applied to skin, then capable of gathering/compressing the skin thereunder upon release of the stretch on the membrane. In addition, the elastically deformable membrane should be sufficiently safe for application to the skin of a patient for long term exposure and should be sufficiently durable for maintaining skin placement for long periods of time. Non-limiting examples of stretchable materials from which the elastically deformable membranes of the present disclosure can be formed include medical, kinesiology, and surgical tapes, such as (but not limited to) TheraBrand kinesiology tape (TheraBand, Akron, OH).

It will be understood that the entirety of the elastically deformable membrane may be formed of a stretchable material, or only a portion of the elastically deformable membrane may be formed of a stretchable material. In the latter instance, the elastically deformable membrane may further be provided with a portion (in combination with the stretchable material) that does not have the ability to stretch or that is reinforced to substantially eliminate the ability to stretch (referred to herein as a "non-stretchable portion" or "non-stretchable material"). These non-stretchable portions may be used, for example but not by way of limitation, at external fixation member insertion sites and/or around incision sites. One non-limiting example of a tape that can function as a non-stretchable material in accordance with the present disclosure is 3M Transpore surgical tape (3M, Maplewood, MN).

Any bonding materials known in the art as being capable of attaching a membrane to the skin of a patient for a sufficient period of time and in a sufficiently safe manner may be used as a bonding material in accordance with the present disclosure. In a particular (but non-limiting) embodiment, the bonding material comprises a skin adhesive or glue.

The term "external fixation member" as used herein refers to any percutaneous device that is capable of being fixated within a patient (i.e., capable of being inserted through the skin and tissue of a patient and into a bone thereof) and to which a distraction force may be applied. Non-limiting examples of external fixation members that may be utilized in accordance with the present disclosure include pins, screws, and wires. These external fixation members may be formed of metallic, polymeric, and/or biodegradable materials.

Methods of separating at least a portion of the membrane so as to release a portion of the tension/compression in the skin are well known in the art, and thus all methods thereof fall within the scope of the present disclosure. In certain non-limiting embodiments, step (F) may include cutting or tearing at least a portion of the membrane. In another non-limiting embodiment, at least a portion of the segment of elastically deformable membrane includes multiple layers and/or weaves of elastically deformable material (wherein the layers/weaves have the same or different levels of tension). In this embodiment, step (F) comprises separating at least one layer or weave of the membrane from the other layers/weaves, thereby releasing a portion of the tension in the membrane.

In certain non-limiting embodiments, the membrane may be provided with score lines or slits (that only extend partially through the membrane) that indicate the points at which the membrane should be separated each time step (F) is performed. These score lines or slits may be placed at any position along the segment; in certain non-limiting embodiments, the initial score lines or slits are placed in close proximity to the insertion site for the external fixation member, and the additional score lines or slits extend toward the middle of the segment.

The viscoelasticity of skin allows for compressing/gathering and stretching of the skin in the manner described herein, and a sufficient amount of compression/gathering and stretch may be obtained almost immediately upon application of the stretched membrane followed by release of the tension thereon, in accordance with the methods described herein. Alternatively, the skin may need to be allowed to compress/gather and stretch over a period of time until a desired amount of compression/stretching is obtained. In addition, placement of a single segment of elastically deformable membrane may not be sufficient to obtain a sufficient amount of gathering/compression of the skin. Thus, steps (A)-(C) may be repeated until a desired level of skin compression/gathering is achieved prior to performing step (D) (as well as any of steps (E)-(G), when present). When multiple segments of elastically deformable membranes are used, the elastically deformable membranes may be formed of the same or different materials (such as (but not limited to) different weaves and/or different elasticities, as well as combination materials (including, for example, nitinol fibers)). In addition, the multiple segments may be the same size or different sizes. Further, placement of the multiple segments may be substantially overlapping, partially overlapping, or substantially non-overlapping. For example (but not by way of limitation), one or more large segments of elastically deformable membrane may first be applied to the skin of the patient, and then one or more smaller segments of elastically deformable membrane may be applied to a small segment of the skin that spans either side of the insertion point for an external fixation member. To engage more skin in morphing, additional segments of elastically deformable membranes may be applied to the surrounding area, away from the insertion points of the external fixation members. This method would additionally allow rotation of skin adhesion sites over time to help the skin recover in between applications.

When steps (A)-(C) are repeated so that multiple segments of stretched membranes have been applied to the skin, step (F) may include (for example, but not by way of limitation) separating at least a portion of one or more of the segments of membranes.

Any of the components of the system may have an antimicrobial agent associated therewith. For example (but not by way of limitation), the segment(s) of elastically deformable membrane may have an antimicrobial agent associated with at least a portion of a surface thereof.

Any antimicrobial agents known in the art or otherwise contemplatable by a person of ordinary skill in the art may be utilized in accordance with the present disclosure. For example (but not by way of limitation), the antimicrobial agent may be an antibacterial agent and/or an antifungal agent. Examples of antimicrobial and antibacterial agents are well known in the art, and a wide variety thereof are commercially available. Therefore, it is well within the common abilities of a person having ordinary skill in the art to identify and select particular antimicrobial and antibacterial agents that can be used in accordance with the present disclosure, given the particular uses for which the skin compression devices are employed. As such, no further discussion thereon is deemed necessary.

In certain non-limiting embodiments, the method further includes the step of placing a tension protector pad on the at least one external fixation member following step (D). The tension protector pad may be substantially rigid, partially flexible, or substantially flexible. The tension protector pad has an opening that extends therethrough and that is capable of receiving a portion of an external fixation member such that the external fixation member extends through the tension protector pad. The tension protector pad may also have a bonding material associated with at least a portion of a surface thereof that attaches the tension protector pad to the membrane (or to the skin, when the external fixation member is inserted through the skin outside of the membrane).

The tension protector pad may be used with or without the elastically deformable membrane; when used without the elastically deformable membrane, the tension protector pad may be attached to another kind of membrane (such as, but not limited to, surgical tape) or may be attached directly to the skin. In addition, the tension protector pad distributes a force exerted by a leading edge of the external fixation device around an area of skin disposed beneath the tension protector pad. In this manner, the tension protector pad(s) transmits the distraction force(s) from the pins to the area of skin, thus bypassing the incision sites. This is an important feature associated with the optional use of these tension protector pads, because minimizing stress at the pin incision sites further reduces morbidity and risk of infections.

It should be understood that the tension protector pads may be formed of one or more materials and may have one or more parts/elements. In addition, the tension protector pads may have one or more access openings, one or more mechanical means of contact or attachment to the external fixation member, and one or more connectors to the skin-contacting portion of the pad, as well as any other mechanical means of achieving the function described in the present disclosure, as will be contemplatable by a person having ordinary skill in the art. Thus, all configurations of pads that can function as tension protector pads as described herein fall within the scope of the present disclosure.

In a particular (but non-limiting) embodiment, the tension protector pad(s) may have at least one of any of the antimicrobial agents described or otherwise contemplated herein associated therewith. For example (but not by way of limitation), the tension protector pad may have a cavity in which the at least one antimicrobial agent is disposed.

One non-limiting example of a commercially available product that may be utilized in conjunction with a tension protector pad in accordance with the present disclosure is Ethicon's BIOPATCH® (Protective disk with Chlorhexidine gluconate, Ethicon, Inc., Somerville, NJ). For example (but not by way of limitation), the BIOPATCH® may be placed inside the cavity of the tension protector pad.

Certain non-limiting embodiments of the present disclosure include a method similar to that described above but further including the placement of two external fixation devices. This method includes the steps of: (A) applying force to a segment of any of the elastically deformable membranes described or otherwise contemplated herein above to stretch the membrane to a stretched length that is greater than an original length of the membrane, wherein the elastically deformable membrane has a bonding material associated with at least a portion of a surface thereof; (B) applying the stretched membrane to a skin of a patient, wherein the bonding material attaches the stretched membrane to the skin; (C) releasing the stretch force on the membrane after application to the skin, thereby causing the skin having the membrane attached thereto to compress/gather; (D) inserting a first external fixation member through the membrane and skin at a location interior to a first end of the membrane (wherein the first external fixation member extends through the skin and tissue of the patient and into a bone of the patient); (E) inserting a second external fixation member through the membrane and skin at a location interior to a second end of the membrane (wherein the first external fixation member extends through the skin and tissue of the patient and into a bone of the patient); (F) applying at least one distraction force to the at least one of the first and second external fixation members, thereby moving the bone(s) with which each external fixation member is associated; (G) separating at least a portion of the membrane so as to release a portion of the tension/compression in the skin at a rate that is similar to a rate at which the distraction force is applied; and (H) repeating steps (F) and (G) over a period of time, thus allowing the skin to move at a rate similar to the external fixation member(s) inserted therethrough.

While steps (D) and (E) above describe insertion of the external fixation members through the elastically deformable membrane, it will be understood that the scope of the present disclosure also includes where one or both of the external fixation members is inserted through the skin at a position outside of the membrane (i.e., through a portion of the skin that does not have the membrane attached thereto).

Similar to the method above, any methods of separating at least a portion of the membrane so as to release a portion of the compression/tension in the skin known in the art or otherwise contemplated herein fall within the scope of the present disclosure. In certain non-limiting embodiments, step (G) may include cutting or tearing at least a portion of the membrane. Alternatively, when at least a portion of the segment of elastically deformable membrane comprises multiple layers/weaves of elastically deformable material (wherein the layers/weaves have the same or different levels of tension), step (G) may include separating at least one layer/weave of the membrane.

Also similar to the method above, the membrane may be provided with score lines or slits (that only extend partially through the membrane) that indicate the points at which the membrane should be separated each time step (G) is performed. These score lines or slits may be placed at any position along the segment; in certain non-limiting embodiments, the initial score lines or slits are placed in close proximity to the insertion site for the external fixation member, and the additional score lines or slits extend toward the middle of the segment.

Also similar to the method above, steps (A)-(C) can be repeated until a desired level of skin compression/gathering is achieved prior to performing steps (D)-(H). In this embodiment, wherein step (G) may include separating at least a portion of one or more of the membranes.

Also similar to the method above, the method may further include the steps of placing a tension protector pad on the first external fixation member following step (D) and placing a tension protector pad on the second external fixation member following step (E), wherein each of the tension protector pads is any of the tension protector pads disclosed or otherwise contemplated herein.

For each of the methods described herein, one or more of the steps may be performed immediately following a prior step, and/or a period of time may pass in between two or more steps. For example (but not by way of limitation), the elastically deformable membrane may be applied to the skin and allowed to gather/stretch/compress the skin for a period of time (such as, but not limited to, about 1, 2, 3, 4, 5, 6, or 7 days or about 1, 2, 3, or 4 weeks, or any range thereof) prior to the surgical placement of the external fixation member(s). Alternatively, the elastically deformable membrane could be applied to the skin during the surgical procedure and thus immediately prior to placement of the external fixation member(s). In yet another embodiment, both of the above are utilized. That is, steps (A) and (B) are performed (and potentially repeated) to allow the skin to stretch/gather/compress for a period of time until a desired level of stretching/gathering/compression is obtained with minimal discomfort; then that membrane is removed, and steps (A) and (B) are repeated immediately prior to placement of the external fixation member(s), so as to ensure that the external fixation member(s) is inserted through a sterile membrane and environment.

Similarly, a sufficient period of time should pass between the individual applications of distraction force to the external fixation device(s), as is well known in the art. Also, as movement of the skin at a rate similar to the external fixation member inserted therethrough is desired, the optional individual steps of separating at least a portion of the membrane may be performed substantially around the same time as the corresponding distraction step. Further, additional separation steps can be performed if additional separation of the membrane is required to all the skin to move at a rate similar to the external fixation member inserted therethrough.

Certain embodiments of the present disclosure are further directed to a kit that includes any of the components discussed in detail herein above or otherwise contemplated herein. For example, the kit may include at least one segment of any of the elastically deformable membranes disclosed or otherwise contemplated herein in combination with at least two tension protector pads as described or otherwise contemplated herein. In addition, the kit may further include at least two external fixation members as described or otherwise contemplated herein.

In a particular (but non-limiting) embodiment, the kit may include a plurality of segments of the elastically deformable membrane. For example (but not by way of limitation), the kit may include a roll of segments of the membrane, wherein one or more of the segments may be removed from the roll for use in the methods described or otherwise contemplated herein.

Certain embodiments of the present disclosure are further directed to a kit that contains at least two tension protector pads as described or otherwise contemplated herein (in the absence of any elastically deformable membranes).

Certain embodiments of the present disclosure are further directed to a system that includes any of the components discussed in detail herein above or otherwise contemplated herein. For example (but not by way of limitation), the system may include at least one segment of any of the elastically deformable membranes disclosed or otherwise contemplated herein in combination with at least two external fixation members as described or otherwise contemplated herein. In addition, the system may further include at least two tension protector pads as described or otherwise contemplated herein. In another non-limiting example, the system may include at least one segment of any of the elastically deformable membranes disclosed or otherwise contemplated herein in combination with at least two tension protector pads as described or otherwise contemplated herein.

In a particular (but non-limiting) embodiment, the system may include a plurality of segments of the elastically deformable membrane. For example (but not by way of limitation), the system may include a roll of segments of the membrane, wherein one or more of the segments may be removed from the roll for use in the methods described or otherwise contemplated herein.

Certain embodiments of the present disclosure are further directed to a system that contains at least two tension protector pads as described or otherwise contemplated herein (in the absence of any elastically deformable membranes).

Turning now to the Drawings, FIG. 1 illustrates the use of a prior art external fixation system 10 and creation of pin tracks 28 during bone distraction. As shown in the upper panel, two external fixation members 12a and 12b (such as, but not limited to, percutaneous pins) are inserted through a skin 14 of a patient at insertions sites 16a and 16b, respectively, and further inserted into a bone that has been partially or completely separated. That is, the external fixation members 12a and 12b are inserted through the skin insertions sites 16a and 16b, respectively, and into two segments 18a and 18b, respectively, of the cut/separated bone of the patient at insertions sites 20a and 20b, respectively.

As shown in the lower panel of FIG. 1, during distraction osteogenesis, a distraction force is applied to each of the external fixation members 12a and 12b in directions 22a and 22b, respectively, so as to slowly pull the two bone segments 18a and 18b, respectively, apart. As the bone segments 18a and 18b are pulled apart, osteogenesis occurs, and new bone 24 is formed in the gap produced by the distraction forces, thus rejoining the bone segments 18a and 18b. In distraction osteogenesis, the distraction forces are applied slowly over time, so as to allow the new bone 24 to grow and harden over time. Typically, this process takes a period of time in a range of from about one month to about six months, such as (but not limited to) about one month, about six weeks, about two months, about three months, about four months, about five months, or about six months, or any other range between two of these values, or even longer, depending on the process.

However, as the distraction forces pull the two bone segments 18a and 18b apart, the external fixation members 12a and 12b move through the skin 14 and cut the skin 14 in the process. That is, an area 26a of the skin 14 around the leading edge of the external fixation member 12a is stretched until the skin 14 cuts or tears and forms a pin track 28a. Likewise, an area 26b of the skin 14 around the leading edge of the external fixation member 12b is stretched until the skin 14 cuts or tears and forms a pin track 28b. As stated above, these pin tracks 28a and 28b are highly prone to infection that can potentially have a devastating effect on the success of the distraction osteogenesis (or any other external fixation procedures in which pin tracks can be formed).

Therefore, the present disclosure is directed to a system and methods that reduce the risk of pin track infection, thus overcoming the defects and disadvantages of the prior art systems. This is accomplished by morphing and/or distributing the tension formed in the skin around the external fixation member insertion sites and thereby reducing the incidence (and/or length) of pin tracks being formed in the skin. One non-limiting embodiment of these systems and methods will now be described with reference to FIGS. 2-8.

Figures 2, 3:
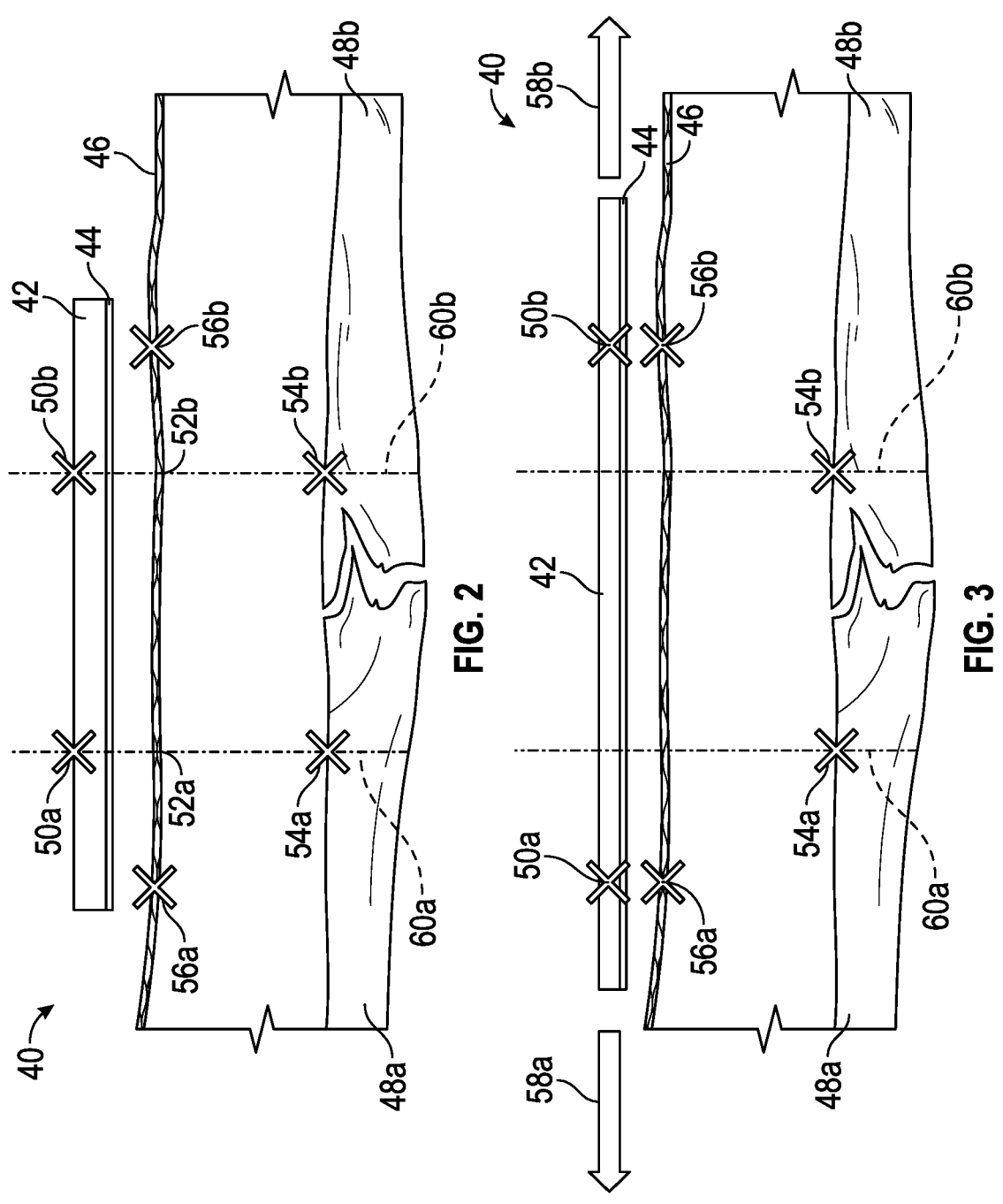
FIG. 2 contains a diagrammatic view of an initial state in the use of a skin morphing and tension distribution system constructed in accordance with the present disclosure.
FIG. 3 contains a diagrammatic view of one step in the use of the system, in which an elastically deformable membrane is stretched and aligned prior to application to the skin of a patient.

In this embodiment of the present disclosure, a system 40 includes an elastically deformable membrane 42 having a bonding material 44 disposed upon at least a portion thereof. The system 40 includes at least one external fixation member 60 (as described in greater detail herein below), and may further optionally include at least one tension protector pad 66 (also as described in greater detail herein below). As shown in FIGS. 2-3, the elastically deformable membrane 42 is aligned with a skin 46 of a patient so as to determine the initial insertion sites for external fixation members in the skin and bone, as well as to determine the final pin locations in the skin following distraction osteogenesis, prior to actual insertion of the external fixation members into the skin. That is, a first insertion site 50a on the elastically deformable membrane 42 is determined that corresponds to a prior art first initial skin insertion site 52a for a first external fixation member 60a (shown in phantom in FIGS. 2-5) that will subsequently be inserted through the skin 46 and into an insertion site 54a in a first segment 48a of a cut/separated bone. Likewise, a second insertion site 50b on the elastically deformable membrane 42 is determined that corresponds to a prior art second initial skin insertion site 52b for a second external fixation member 60b (shown in phantom in FIGS. 2-5) that will subsequently be inserted through the skin 46 and into an insertion site 54b in a second segment 48b of the cut/separated bone.

Then, based upon the desired length of bone to be grown during distraction osteogenesis and the corresponding movement of the external fixation members 60a and 60b through the skin 46, a final skin location site 56a of the first external fixation member 60a in the skin 46 is determined, and a final skin location site 56b of the second external fixation member 60b in the skin 46 is determined. As shown in FIG. 3, at least one force is then applied to the elastically deformable membrane 42 in at least one of directions 58a and/or 58b to stretch the elastically deformable membrane 42 so as to approximately or substantially align the first insertion site 50a on the elastically deformable membrane 42 with the final skin location site 56a and to approximately or substantially align the second insertion site 50b on the elastically deformable membrane 42 with the final skin location site 56b.

While FIG. 3 depicts the elastically deformable membrane 42 as being stretched in both directions 58a and 58b, it will be understood that the same or similar effect can also be achieved by only pulling the elastically deformable membrane 42 in one of the directions 58a or 58b while stretching the membrane about twice the distance in that single direction. That is, one end of the elastically deformable membrane 42 can be held taut while the other end of the elastically deformable membrane 42 is pulled in the direction 58a or 58b until the insertion sites 50a and 50b are approximately or substantially aligned with the final skin location sites 56a and 56b, respectively.

Figures 4, 5:
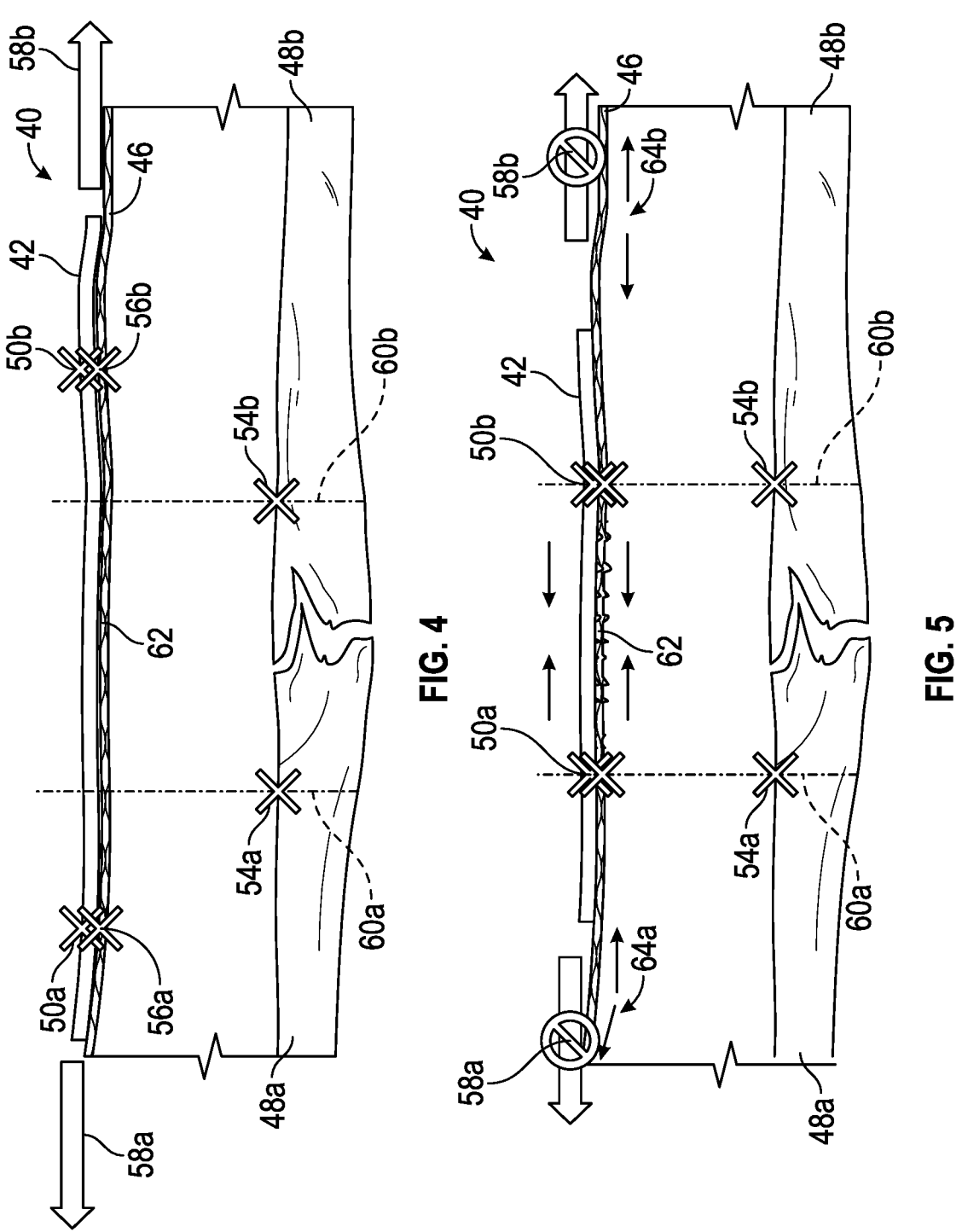
FIG. 4 contains a diagrammatic view of another step in the use of the system, in which the stretched membrane is applied to the skin.
FIG. 5 contains a diagrammatic view of another step in the use of the system, in which the skin to which the membrane is applied gathers/compresses.

Once the insertion sites 50a and 50b of the elastically deformable membrane 42 are approximately or substantially aligned with the final skin location sites 56a and 56b, respectively, the stretch in the membrane 42 is maintained while the stretched membrane 42 is applied (under tension) to the skin 46, as shown in FIG. 4. Upon adherence of the stretched membrane 42 to the skin 46, the stretch force(s) 58a and/or 58b are released. This causes the elastically deformable membrane 42 to contract or shrink back to a length that is approximately the same or substantially similar to its original length, while also causing a portion 62 of the skin 46 to which the membrane 42 is attached to gather and/or compress, as shown in FIG. 5. In addition, contraction of the elastically deformable membrane 42 following application to the skin 46 will also cause stretching of portions 64a and 64b of the skin 46 that are positioned on either side of the portion 62 of skin 46 to which the membrane 42 is attached.

Figures 6, 7:
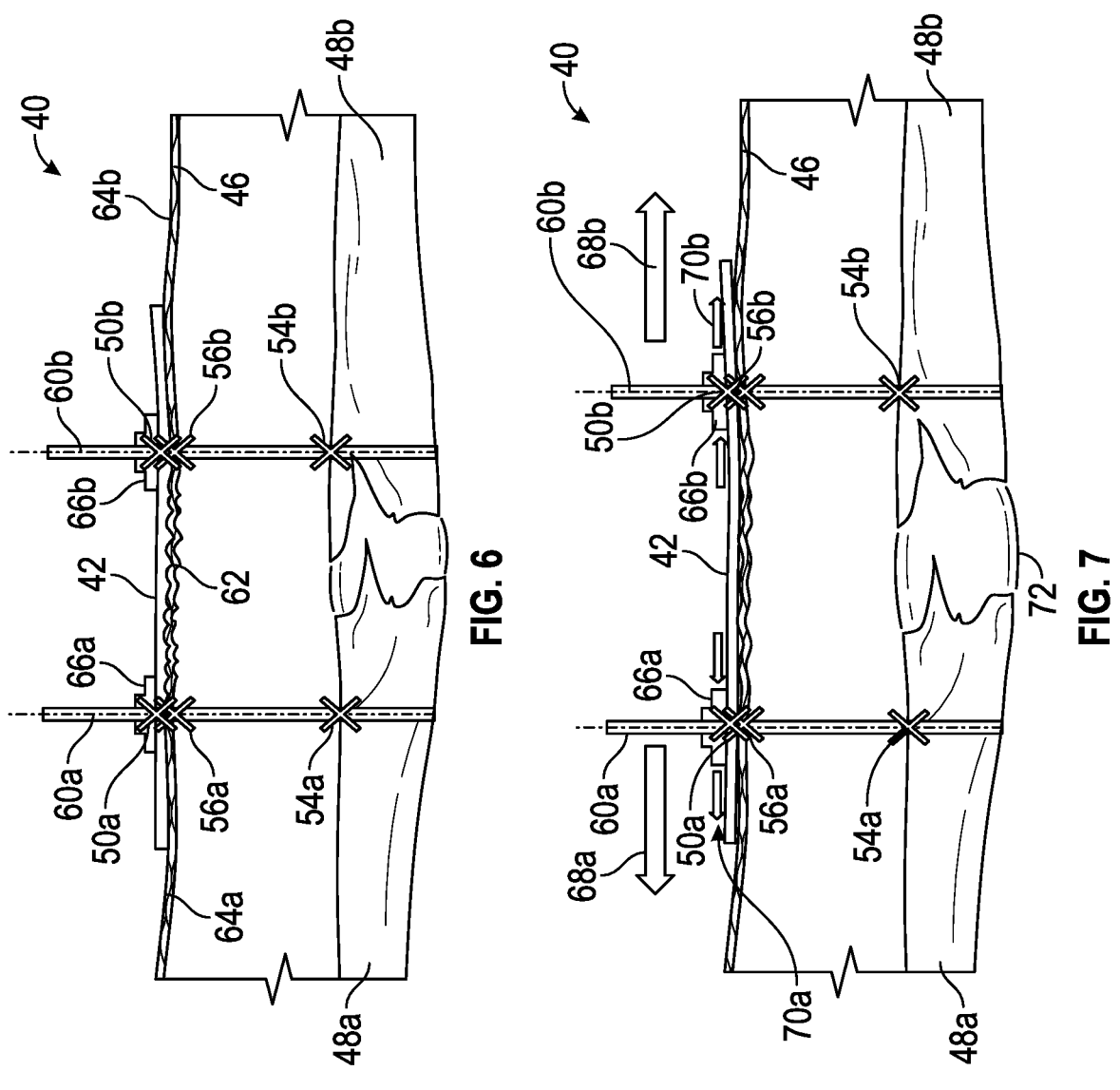
FIG. 6 contains a diagrammatic view of another step in the use of the system, in which two external fixation devices are inserted through the skin and into the bone of the patient.
FIG. 7 contains a diagrammatic view of another step in the use of the system, in which distraction forces are applied to the two external fixation devices.

As shown in FIG. 6, the external fixation members 60a and 60b are then inserted through the skin 46 and into the bone segments 48a and 48b, respectively. However, unlike the prior art methods that insert the external fixation members into the skin at an initial position and then pull the external fixation members through the skin (while cutting/tearing the skin in the process) until a final pin location in the skin is achieved, the present system 40 allows the external fixation members 60a and 60b to be inserted through the skin 46 at a position corresponding to a final pin location, thus preventing the need for the external fixation members 60a and 60b to move (and thus cut/tear) through the skin and form pin tracks. That is, as shown in FIG. 6, the first external fixation member 60a is inserted through the first insertion site 50a in the membrane 42, the final skin location site 56a in the skin 46, and the insertion site 54a in the bone segment 48a. Likewise, the second external fixation member 60b is inserted through the second insertion site 50b in the membrane 42, the final skin location site 56b in the skin 46, and the insertion site 54b in the bone segment 48b.

Figure 8:
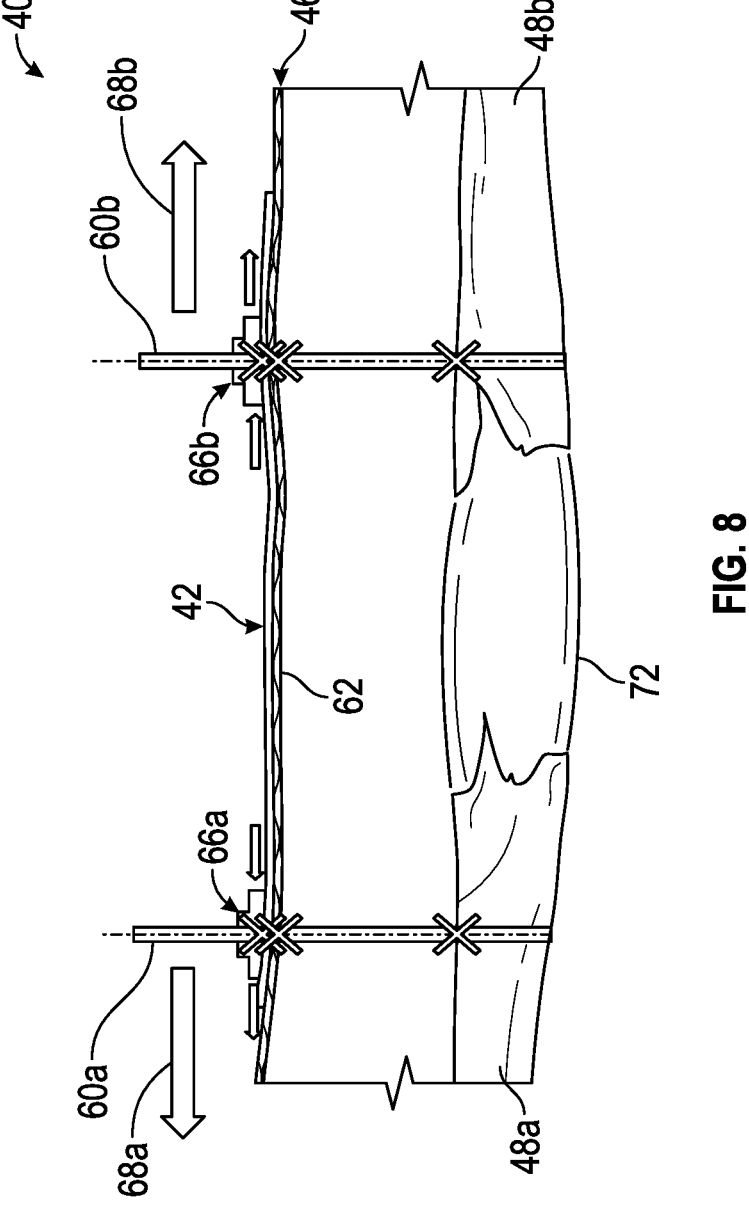
FIG. 8 contains a diagrammatic view of another stage in the use of the system.

Then as shown in FIGS. 7-8, a distraction force is applied to each of the external fixation members 60a and 60b in directions 68a and 68b, respectively, so as to slowly pull the two bone segments 48a and 48b, respectively, apart. As the bone segments 48a and 48b are pulled apart, osteogenesis occurs, and new bone 72 is formed in the gap produced by the distraction forces, thus eventually rejoining the bone segments 48a and 48b and lengthening the bone. In distraction osteogenesis, the distraction forces are applied slowly over time, so as to allow the new bone 72 to grow and harden over time (and thereby increasing the length of the bone). Typically, this process takes a period of time in a range of from about one month to about six months, such as (but not limited to) about one month, about six weeks, about two months, about three months, about four months, about five months, or about six months, or any other range between two of these values, or even longer, depending on the process.

While the bone segments 48a and 48b are moving in response to the distraction forces 68a and 68b, the tension in the portion 62 of skin 46 under the membrane 42 releases over time (either naturally or intentionally through a separation of a portion of the membrane 42), thus allowing the insertions sites 56a and 56b in the skin to travel with the external fixation members 60a and 60b during distraction without cutting or tearing the skin 46 and forming pin tracks therein, and thus avoiding the infections associated therewith. As such, once the distraction process ends, the skin 46 may be approximately or substantially restored to its original shape.

The release of tension in the skin 46 during distraction osteogenesis can occur naturally over time; optionally, one or more portions of the membrane 42 may be separated at one or more time points to cause a specific release of the tension in the portion 62 of the skin 46 at a rate that is somewhat similar to the rate at which the distraction forces 68a and 68b are being applied. Various non-limiting embodiments of membranes that can be utilized to achieve this specific tension release are described in detail herein.

To further distribute the stress imposed by the external fixation members on skin insertion sites, the system 40 may optionally include one or more tension protector pads that distributes a force exerted by a leading edge of each of the external fixation devices around an area of skin disposed beneath the tension protector pad, thereby transmitting the distraction force(s) from the pins/external fixation members to the area of skin through which the force is distributed and thus bypassing the incision sites. This is an important feature associated with the optional use of these tension protector pads, because minimizing stress at the pin incision sites further reduces morbidity and risk of infections.

For example, FIGS. 6-8 illustrates that each of a pair of tension protector pads 66a and 66b is slid down a length of the corresponding external fixation member 60a and 60b, respectively, until each of the tension protector pads 66a and 66b engages the membrane 42. Each of the tension protector pads 66a and 66b is then adhered to the membrane 42 using any of the bonding materials described or otherwise contemplated herein. As the distraction forces 68a and 68b are applied in FIGS. 7-8, these distraction forces 68a and 68b are transmitted from the external fixation members 60a and 60b, respectively, through the tension protector pads 66a and 66b and distributed through the membrane 42 and the skin disposed under the pads 66a and 66b; distribution of the distraction forces 68a and 68b in this manner further reduces the amount of force felt by the skin insertion sites 56a and 56b and further protects the skin insertion sites 56a and 56b from cutting/tearing.

Figure 9:
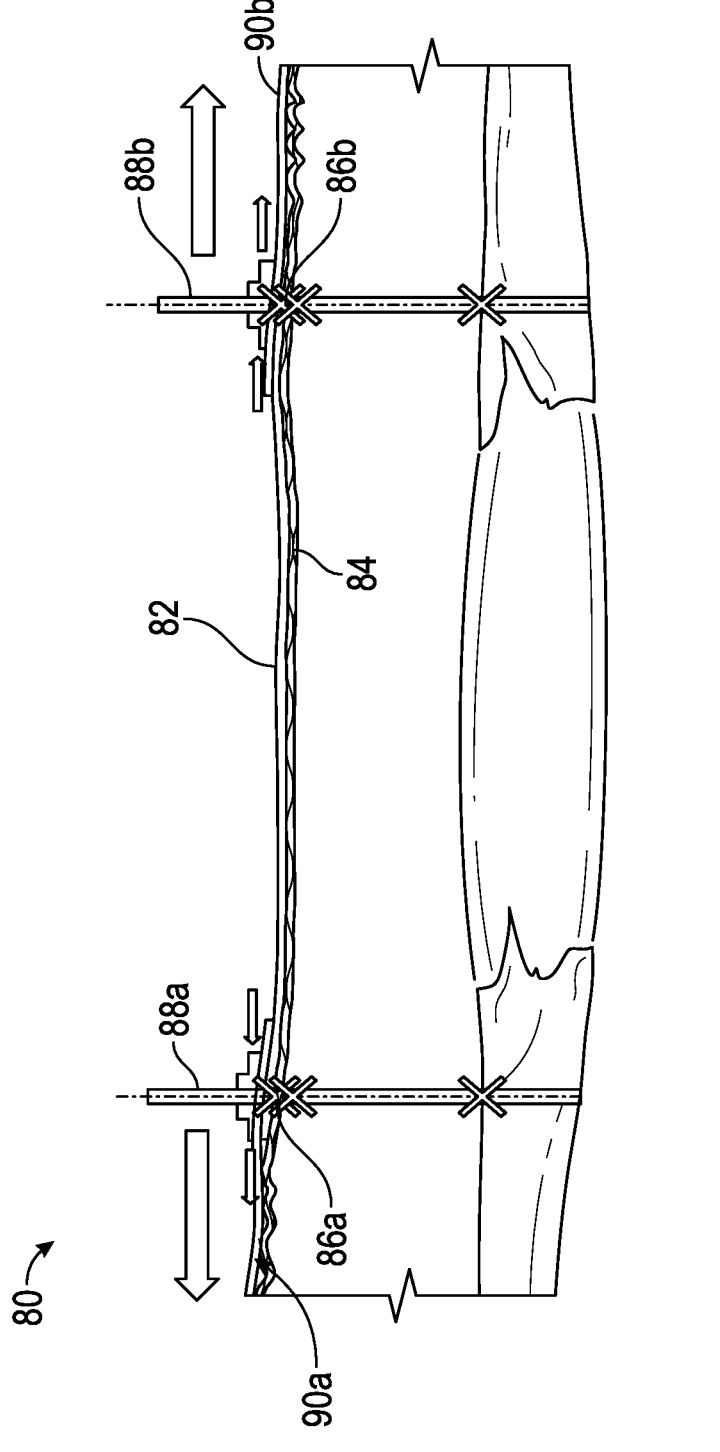
FIG. 9 is a diagrammatic view of the placement of another embodiment of a system constructed in accordance with the present disclosure.

Placement of a single segment of elastically deformable membrane may not be sufficient to obtain a sufficient amount of gathering/compression of the skin. Thus, FIG. 9 illustrates another embodiment of a system 80 constructed in accordance with the present disclosure. The system 80 is similar to the system 40 shown in FIGS. 2-8, except that the system 80 includes three elastically deformable members. A first elastically deformable membrane 82 is disposed on a skin 84 of a patient in a similar manner to the elastically deformable membrane 42 (i.e., by stretching, alignment, and application of the membrane 82 in the stretched condition, then releasing the membrane 82 to compress the portion of skin 84 attached thereto). Then to achieve a greater amount of gathering/compression of the skin 84 around insertion sites 86a and 86b through which external fixation members 88a and 88b will subsequently be inserted through the skin 84, a second elastically deformable membrane 90a is stretched and applied to the skin 84 about the first insertion site 86a (thus causing compression of the portion of skin to which the membrane 90a is applied), while a third elastically deformable membrane 90b is stretched and applied to the skin 84 about the second insertion site 86b (and thus causing compression of the portion of skin to which the membrane 90b is applied). In this manner, the second and third elastically deformable membranes 90a and 90b function to aid with the overstretch of the skin 84 and thereby prevent the formation of pin tracks in the skin 84.

Figure 10:
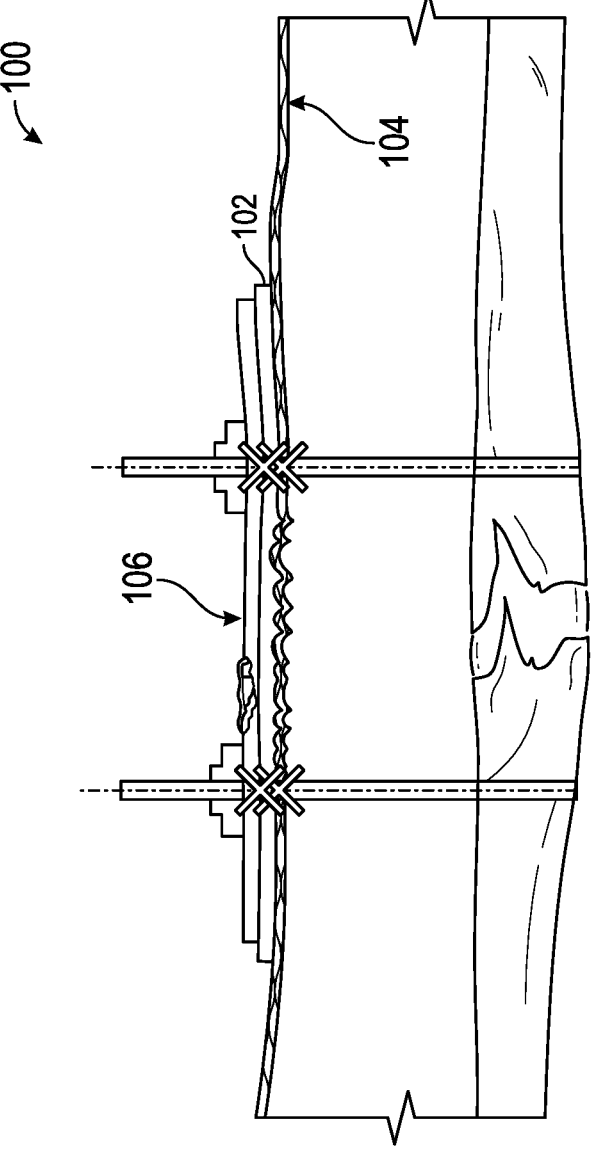
FIG. 10 is a diagrammatic view of the placement of yet another embodiment of a system constructed in accordance with the present disclosure.

In certain non-limiting embodiments of the present disclosure, multiple segments of stretched membranes may be applied to the skin, for example (but not by way of limitation) to gradually stretch the skin to yield a larger stretch distance than would be obtained with a single segment of membrane. As shown in FIG. 10, a system 100 is similar to the systems 40 and 80 described with reference to FIGS. 2-8 and 9, respectively, except that the system 100 includes the use of two elastically deformable membranes similar to the membranes described herein above. A first elastically deformable membrane 102 is stretched, aligned, and applied to a skin 104 of a patient in the manner described herein above. Then a second elastically deformable membrane 106 is stretched, aligned, and applied to the first elastically deformable membrane 102. The second membrane 106 may serve one or both of two functions. First, as described herein above, the combination of the first and second membranes 102 and 106 may provide a larger compression/stretch distance than would be provided by the first membrane 102 alone. Second, the second membrane 106 may serve to provide a separation point for gradually releasing a portion of the tension on the skin 104 and thereby control the rate of release of the compression of the skin. That is, the first and second membranes 102 and 106 essentially function as multiple layers of a single structure, wherein at least a portion of one layer can be cut or separated to control the rate of release of a portion of the tension in the skin 104.

When multiple segments of elastically deformable membranes are used (as in FIGS. 9-10), the segments of elastically deformable membranes may be formed of the same or different materials (such as different weaves). In addition, the multiple segments may be substantially the same size (as in FIG. 10) or different sizes (as in FIG. 9). Further, placement of the multiple segments may be substantially overlapping (as in FIG. 10), partially overlapping (as in FIG. 9), or substantially non-overlapping (such as the use of membranes 90*a* and 90*b* in the absence of membrane 82 in FIG. 9). One or more large segments of elastically deformable membrane may first be applied to the skin of the patient (such as the two large segments in FIG. 10) and/or one or more smaller segments of elastically deformable membrane may be applied to a small segment of the skin that spans either side of the insertion point for an external fixation member (i.e., membranes 90*a* and 90*b* in FIG. 9). While FIGS. 9-10 illustrate the use of two or three layers/segments of elastically deformable membranes, it will be understood that the elastically deformable membranes may include four or more layers/segments to further increase the amount of stretch/compression of the skin and/or further control the rate of skin tension release upon separation of at least a portion thereof.

FIGS. 11A-C illustrate application of an elastically deformable membrane in accordance with the methods described herein. In FIG. 11A, a first elastically deformable membrane 120 is stretched to provide a length of about 109 mm between two pin insertion sites 122*a* and 122*b* of a patient's skin 124. In FIG. 11B, the stretched first membrane 120 is applied to the skin 124 and allowed to contract to its original shape, while a second elastically deformable membrane 126 is then stretched, applied to the skin 124 and/or the first membrane 120, and allowed to contract to its original shape. Upon contraction of the first and second membranes 120 and 126, the length of skin 124 between the two pin insertion sites 122*a* and 122*b* is reduced to about 87 mm (i.e., an about 22 mm decrease in length due to the compression of the skin 124 underneath the two membranes 120 and 126). Then in FIG. 11C, when both the first and second membranes 120 and 126 are peeled back (via cutting or tearing), the length of skin 124 between the two pin insertion sites 122*a* and 122*b* returns to a length of about 103 mm, which is substantially similar to the original length of about 109 mm. In other words, the skin 124 between the two pin insertion sites 122*a* and 122*b* compressed/gathered about 22 mm during the compression process of the methods of the present disclosure and then traveled about 16 mm during the distraction process of the methods of the present disclosure.

Figure 12:
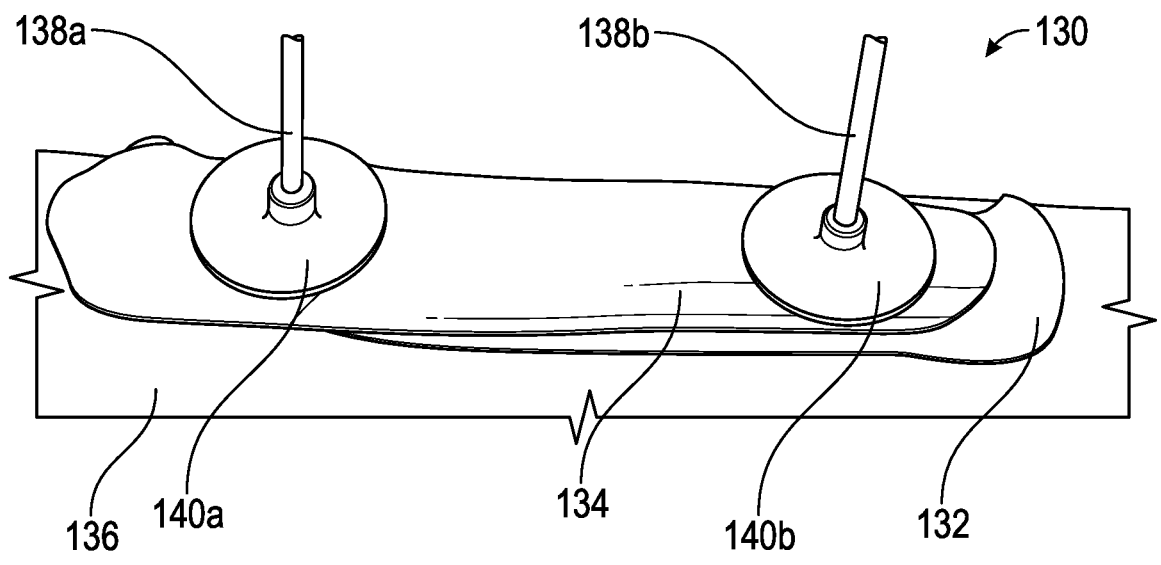
FIG. 12 is a perspective view illustrating another embodiment of a system constructed in accordance with the present disclosure and applied to the skin of a patient.
Figure 13:
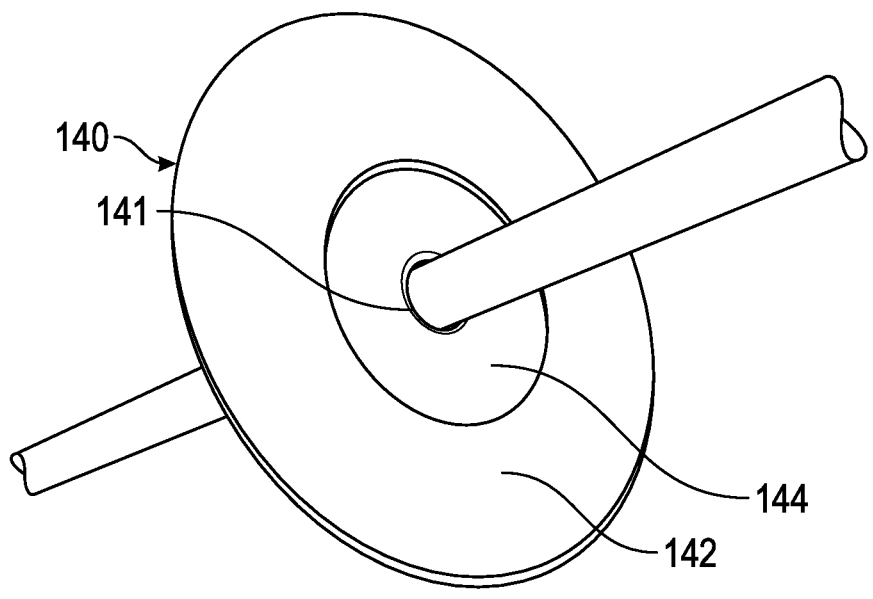
FIG. 13 is a perspective view illustrating a tension protector pad of the system of FIG. 12.

FIG. 12 illustrates a system 130 substantially similar to the systems described herein previously. The system 130 includes two elastically deformable membranes 132 and 134 that are each applied to a skin 136 of a patient in the manner described herein above (i.e., stretching, alignment, and application in the stretched condition, followed by release thereof to compress a portion of skin attached thereto). Then a pair of external fixation members 138*a* and 138*b* are inserted through the membranes 132 and 134, through the skin 136, and into bone segments there below (not shown). In addition, a tension protector pad 140*a* or 140*b* is slid down a corresponding external fixation member 138*a* or 1438*b*, respectively, until the tension protector pads 140*a* and 140*b* engage the membrane 134. As shown in FIG. 13, each of the tension protector pads 140 has an opening 141 through which the external fixation member is inserted. Each of the tension protect pads 140 may also include a bonding material 142 disposed on at least a portion of a surface thereof that attaches the tension protector pad 140 to the membrane 134. As described herein above, these tension protector pads function to transmit the distraction force from the external fixation member to the skin, thereby bypassing the incision site and thus reducing morbidity and the risk of infection.

In addition, as shown in FIG. 13, each of the tension protector pads 140 may optionally have a cavity 144 formed therein in which, for example, an antimicrobial agent may be disposed, as described herein above. This antimicrobial agent functions to further reduce morbidity and the risk of infection during distraction osteogenesis.

While the embodiments shown in the Drawings illustrate the systems of the present disclosure being utilized with external fixation in combination with distraction osteogenesis, it will be understood that the systems and methods disclosed herein are not limited to use with distraction osteogenesis. That is, as described herein above, pin tracks can be formed simply as the result of patient movement when an external fixation system is in place, or even as a result of gravity or slight movement of the external fixation system. Therefore, the scope of the present disclosure explicitly includes devices, systems, and methods that can be utilized with any external fixation mechanisms known in the art or otherwise contemplated herein where pin tracks can potentially be formed and, as such, are at risk of infection.

Thus, in accordance with the present disclosure, there have been provided devices, assemblies, and kits, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A method, comprising the steps of:

(A) applying force to a segment of an elastically deformable membrane to stretch the elastically deformable membrane to a stretched length that is greater than an original length of the elastically deformable membrane, wherein the elastically deformable membrane has a bonding material associated with at least a portion of a surface thereof;

(B) applying the stretched length of elastically deformable membrane to a skin of a patient, wherein the bonding material attaches the stretched length of elastically deformable membrane to the skin;

(C) releasing the force on the elastically deformable membrane after application to the skin, thereby causing the skin having the elastically deformable membrane attached thereto to compress;

(D) inserting at least one external fixation member through the skin at a location outside of the elastically deformable membrane;

(E) applying at least one distraction force to the at least one external fixation member; and (F) separating at least a portion of the elastically deformable membrane so as to release a portion of the tension in the skin at a rate that is similar to a rate at which the distraction force is applied.

2. The method of claim 1, further comprising the step of:

(G) repeating steps (E) and (F) over a period of time, thus allowing the skin to move at a rate similar to the external fixation member inserted therethrough.

3. The method of claim 1, wherein at least a portion of the segment of elastically deformable membrane comprises a plurality of layers and/or weaves of elastically deformable material.

4. The method of claim 1, wherein at least a portion of the segment of elastically deformable membrane is formed of a substantially non-stretchable material.

5. The method of claim 1, wherein the segment of elastically deformable membrane has an antimicrobial agent associated with at least a portion of a surface thereof.

6. The method of claim 1, further comprising the steps of:

placing a tension protector pad on the at least one external fixation member following step (D), wherein the tension protector pad has an opening extending therethrough for receiving a portion of the external fixation member, and wherein the tension protector pad has a bonding material associated with at least a portion of a surface thereof; and attaching the tension protector pad to the skin of the patient about the insertion site for the external fixation member via the bonding material.

7. The method of claim 6, wherein the tension protector pad has at least one antimicrobial agent associated therewith.

8. The method of claim 7, wherein the tension protector pad has a cavity in which the at least one antimicrobial agent is disposed.

\* \* \* \* \*